(12) United States Patent
Allen-Hoffmann et al.

(10) Patent No.: US 7,462,448 B2
(45) Date of Patent: Dec. 9, 2008

(54) SPECIES SPECIFIC DNA DETECTION

(75) Inventors: Lynn Allen-Hoffmann, Madison, WI (US); John M. Centanni, Madison, WI (US)

(73) Assignee: Stratatech Corporation, Madison, WI (US)

( * ) Notice: Subject to any disclaimer, the term of this patent is extended or adjusted under 35 U.S.C. 154(b) by 414 days.

(21) Appl. No.: 10/633,141

(22) Filed: Aug. 1, 2003

(65) Prior Publication Data

US 2004/0146881 A1 Jul. 29, 2004

Related U.S. Application Data

(60) Provisional application No. 60/400,726, filed on Aug. 2, 2002.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.31; 536/24.33

(58) Field of Classification Search .................. None
See application file for complete search history.

(56) References Cited

U.S. PATENT DOCUMENTS

| | | | |
|---|---|---|---|
| 4,485,096 A | 11/1984 | Bell | |
| 4,683,195 A | 7/1987 | Mullis et al. | |
| 4,683,202 A | 7/1987 | Mullis | |
| 4,965,188 A | 10/1990 | Mullis et al. | |
| 5,011,769 A | 4/1991 | Duck et al. | |
| 5,124,246 A | 6/1992 | Urdea et al. | |
| 5,288,609 A | 2/1994 | Engelhardt et al. | |
| 5,403,711 A | 4/1995 | Walder et al. | |
| 5,409,818 A | 4/1995 | Davey et al. | |
| 5,474,796 A | 12/1995 | Brennan | |
| 5,536,656 A | 7/1996 | Kemp et al. | |
| 5,538,848 A | 7/1996 | Livak et al. | |
| 5,597,694 A | 1/1997 | Munroe et al. | |
| 5,624,802 A | 4/1997 | Urdea et al. | |
| 5,660,988 A | 8/1997 | Duck et al. | |
| 5,693,332 A | 12/1997 | Hansbrough | |
| 5,710,264 A | 1/1998 | Urdea et al. | |
| 5,792,614 A | 8/1998 | Western et al. | |
| 5,843,780 A | 12/1998 | Thomson | |
| 5,846,717 A | 12/1998 | Brow et al. | |
| 5,849,481 A | 12/1998 | Urdea et al. | |
| 5,851,770 A | 12/1998 | Babon et al. | |
| 5,858,659 A | 1/1999 | Sapolsky et al. | |
| 5,882,856 A | 3/1999 | Shuber | |
| 5,882,867 A | 3/1999 | Ullman et al. | |
| 5,914,230 A | 6/1999 | Liu et al. | |
| 5,919,626 A | 7/1999 | Shi et al. | |
| 5,925,525 A | 7/1999 | Fodor et al. | |
| 5,952,174 A | 9/1999 | Nikiforov et al. | |
| 5,958,692 A | 9/1999 | Cotton et al. | |
| 5,968,546 A | 10/1999 | Baur et al. | |
| 5,985,551 A | 11/1999 | Brennan | |
| 5,985,557 A | 11/1999 | Prudent et al. | |
| 5,989,837 A | 11/1999 | Allen-Hoffmann et al. | |
| 5,994,069 A | 11/1999 | Hall et al. | |
| 6,001,311 A | 12/1999 | Brennan | |
| 6,001,567 A | 12/1999 | Brow et al. | |
| 6,013,170 A | 1/2000 | Meade | |
| 6,017,696 A | 1/2000 | Heller | |
| 6,039,760 A | 3/2000 | Eisenburg | |
| 6,045,996 A | 4/2000 | Cronin et al. | |
| 6,051,380 A | 4/2000 | Sosnowski et al. | |
| 6,063,573 A | 5/2000 | Kayyem | |
| 6,068,818 A | 5/2000 | Ackley et al. | |
| 6,090,543 A | 7/2000 | Prudent et al. | |
| 6,110,677 A | 8/2000 | Western et al. | |
| 6,110,684 A | 8/2000 | Kemper et al. | |
| 6,121,001 A | 9/2000 | Western et al. | |
| 6,150,097 A | 11/2000 | Tyagi et al. | |
| 6,183,960 B1 | 2/2001 | Lizardi | |
| 6,200,806 B1 | 3/2001 | Thomson | |
| 6,210,884 B1 | 4/2001 | Lizardi | |
| 6,214,567 B1 | 4/2001 | Allen-Hoffmann et al. | |
| 6,221,583 B1 | 4/2001 | Kayyoem et al. | |
| 6,245,566 B1 | 6/2001 | Gearhart et al. | |
| 6,248,229 B1 | 6/2001 | Meade | |
| 6,258,998 B1 | 7/2001 | Damiani et al. | |
| 6,326,198 B1 | 12/2001 | Emerson et al. | |
| 6,924,141 B2 * | 8/2005 | Morgan et al. | ............... 435/325 |

FOREIGN PATENT DOCUMENTS

| | | |
|---|---|---|
| EP | 0 689 591 B1 | 6/1997 |
| WO | WO 99/67641 | 12/1999 |
| WO | WO 00/12682 | 3/2000 |
| WO | WO 00/27995 | 5/2000 |
| WO | WO 00/39587 | 7/2000 |
| WO | WO 00/52145 | 9/2000 |
| WO | WO 00/73421 | 12/2000 |
| WO | WO 01/00650 | 1/2001 |
| WO | WO 01/53465 | 7/2001 |
| WO | WO 01/68815 | 9/2001 |
| WO | WO 01/96532 | 12/2001 |

OTHER PUBLICATIONS

Edwards, M.C. et al. PCR Methods and Applications 3:65-75 (1994).*

(Continued)

*Primary Examiner*—Diana B Johannsen

(57) ABSTRACT

The present invention relates to methods and compositions for the identification of species-specific material in pharmaceutical products. In particular, the present invention relates to methods for the identification of species-specific DNA in a population of a different species or following contact (e.g., growth) with cells of a different species.

23 Claims, No Drawings

OTHER PUBLICATIONS

Boyle, A.L. et al. Genomics 12(3):517-525 (1992).*
Ahern, Scientist 9:20 (1995).
Martin and Evans, Proc. Natl. Acad. Sci USA 72:1441-1445 [1975].
Meana et al., Burns 24:621-30 (1998).
Baden, In Vitro Cell. Dev. Biol. 23(3):205-213 (1987).
Boucamp et al., J. cell. Biol., 106:761-771 (1988).
Allen-Hoffmann et al., J. Invest. Dermatol., 114(3): 444-455 (2000).

* cited by examiner

SPECIES SPECIFIC DNA DETECTION

This application claims the benefit of U.S. Provisional Application 60/400,726, filed Aug. 2, 2002.

FIELD OF THE INVENTION

The present invention relates to methods and compositions for the identification of species-specific material in pharmaceutical products. In particular, the present invention relates to methods for the identification of species-specific DNA in a population of a different species or following contact (e.g., growth) with cells of a different species.

BACKGROUND OF THE INVENTION

There is a substantial market for burn therapy and for the repair or support of appropriate epithelial tissues and other wound and skin closure products. For example, venous leg ulcers affect about 1 million people in the United States and 3 million worldwide, and other ulcer conditions such as diabetic ulcers and pressure ulcers (bedsores), affect approximately 10 million people worldwide. Venous ulcer standard care can take over 6 months to heal a wound and cost in excess of $10,000. Furthermore, foot ulcers are a leading cause of hospitalization among diabetics and are estimated to cost the U.S. healthcare system over $1 billion annually. Estimates for hospitalizations for burns in the United States range from 60,000 to 80,000 annually, and costs for recovery from acute injuries range from $36,000 to $117,000 per patient. Human skin equivalent cultures are commonly used in such applications.

Much interest is currently being expressed in the use of stem cells for a variety of tissue replacement therapies. These therapies may be effective for millions of people suffering from diseases ranging from diabetes and sclerosis of the liver to Parkinson's disease and multiple sclerosis.

Mouse 3T3 fibroblast cells are extensively used as feeder layers to enhance the cultivation of human keratinocyte in vitro. Once inactivated to inhibit their proliferation, 3T3 cells are used as a mitotically inactivated "feeder layer" of fibroblasts. Stem cells are also commonly grown on feeder cell layers in vitro. Stem cells depend on cytokines and other factors produced by the feeder cells to prevent differentiation.

However, it is undesirable to have mouse cells remaining in products for use in humans. Such cells can lead to allergic reactions and rejection of transplanted cells. Their presence in a therapeutic product also increases the potential of exposure to xenobiotic pathogens. Thus, robust, sensitive, and accurate methods of detecting contaminating mouse cells in human cell cultures are needed.

SUMMARY OF THE INVENTION

The present invention relates to methods and compositions for the identification of species-specific material in pharmaceutical products. In particular, the present invention relates to methods for the identification of species-specific DNA in a population of a different species or following contact (e.g., growth) with cells of a different species.

Accordingly, in some embodiments, the present invention provides a method for detecting species-specific nucleic acid, comprising providing a sample selected from the group including, but not limited to, a first cell sample from a first species or a cell product derived from the first cell sample, wherein the sample has had previous exposure to second cells from a second species or a cell product derived from the second cells; first nucleic acid probes specific for nucleic acid derived from the second species; exposing the sample to the first nucleic acid probes under conditions such that the first nucleic acid probes hybridize to the nucleic acid derived from the second species and do not hybridize to nucleic acid from said second species, thereby facilitating the detection of the nucleic acid derived from the second species. In some embodiments, the nucleic acid probes are specific for a repetitive element of nucleic acid derived from the second species. In preferred embodiments, the repetitive element is present in at least 20 copies, preferably at least 40 copies, even more preferably at least 60 copies, and still more preferably at least 80 copies. In some embodiments, the first cell sample is a human cell sample. In other embodiments, the first cell sample is a primate cell sample. In some embodiments, the second cell sample is a mouse cell sample. In other embodiments, the second cell sample is selected from the group including, but not limited to, a rat cell sample and a porcine cell sample. In some embodiments, the exposing comprises PCR. In some embodiments, the nucleic acid probes are PCR primers. In other embodiments, the exposing comprises a hybridization assay selected from the group including, but not limited to, a Southern blot assay, a microarray assay, and an enzymatic detection of hybridization assay.

In some embodiments, the method further comprises the step of exposing the sample to second nucleic acid probes, wherein the second nucleic acid probes are specific for a nucleic acid derived from the sample. In some embodiments, the first nucleic acid probes and the second nucleic acid probes are PCR primers, and the exposing comprises PCR, wherein the PCR is a multiplex PCR reaction. In some embodiments, the first nucleic acid probes are selected from the group including, but not limited to, SEQ ID NOs: 1, 2, and 5-26. In some embodiments, the second nucleic acid probes are selected from the group including, but not limited to, SEQ ID NOs: 3 and 4.

In some embodiments, the sample is a cultured human skin tissue. In certain embodiments, the human skin tissue comprises keratinocytes selected from the group consisting of primary keratinocytes and immortalized keratinocytes (e.g., NIKS cells). In certain embodiments, the first cell sample comprises stem cells (e.g., including, but not limited to, embryonic stem cells and adult stem cells). In some embodiments, the second cells comprise feeder cells (e.g., mouse fibroblast cells).

The present invention additionally provides a kit, comprising a sample selected from the group consisting of a first cell sample from a first species or a cell product derived from the first cell sample, wherein the sample has had previous exposure to second cells from a second species or a cell product derived from the second cells; first nucleic acid probes specific for nucleic acid derived from the first species; second nucleic acid probes specific for nucleic acid derived from the second species; and instructions for using the first and second nucleic acid probes for determining the presence or absence of nucleic acid from the second species in the first cell sample. In some embodiments, the nucleic acid probes are specific for a repetitive element of nucleic acid derived from the second species. In preferred embodiments, the repetitive element is present in at least 20 copies, preferably at least 40 copies, even more preferably at least 60 copies, and still more preferably at least 80 copies.

In some embodiments, the first cell sample is a human cell sample. In other embodiments, the first cell sample is a human or non-human cell sample. In some embodiments, the second cell sample includes, but in not limited to, a mouse cell sample, a rat cell sample and a porcine cell sample. In some embodiments, the second cell sample comprises feeder cells (e.g., mouse fibroblast cells).

In some embodiments, the first and second nucleic acid probes are PCR primers. In some embodiments, the second nucleic acid probes are selected from the group including, but not limited to, SEQ ID NOs: 1, 2, and 5-26. In some embodiments, the first nucleic acid probes are selected from the group including, but not limited to, SEQ ID NOs: 3 and 4. In some embodiments, the human cell sample is keratinocytes. In other embodiments, the first cell sample is a stem cell sample (e.g., including, but not limited to, embryonic stem cells and adult stem cells).

In still further embodiments, the present invention provides a method of detecting species specific nucleic acid, comprising providing a sample selected from the group consisting of a cell sample from a first species or a cell product derived from the cell sample; first nucleic acid probes specific for nucleic acid derived from the cell sample; and exposing the sample to the first nucleic acid probes under conditions such that the first nucleic acid probes hybridize to the nucleic acid derived from the cell sample, thereby facilitating the detection of the nucleic acid derived from the cell sample. In some embodiments, the nucleic acid probes are specific for a repetitive element of nucleic acid derived from the first species. In preferred embodiments, the repetitive element is present in at least 20 copies, preferably at least 40 copies, even more preferably at least 60 copies, and still more preferably at least 80 copies. In some embodiments, the sample is a derived from an organism including, but not limited to, human, primate, mouse, porcine, and rat. In some embodiments, the exposing further comprises quantitating the amount of nucleic acid in the sample. For example, in some embodiments, quantitating comprises quantitating the change in amount of the nucleic acid over time. In some embodiments, the exposing comprises PCR and the nucleic acid probes are PCR primers. In other embodiments, the exposing comprises a hybridization assay selected from the group consisting of a Southern blot assay, a microarray assay, and an enzymatic detection of hybridization assay. In some embodiments, the nucleic acid probes are selected from the group including, but not limited to, SEQ ID NOs: 1-26.

DEFINITIONS

As used herein, the term "cultured skin tissue" refers to "skin equivalents" and "skin substitutes." As used herein, the terms "skin equivalent" and "skin substitute" are used interchangeably to refer to an in vitro derived culture of keratinocytes that has stratified into squamous epithelia. Typically, the skin equivalents are produced by organotypic culture.

As used herein, the term "organotypic" culture refers to a three-dimensional tissue culture where cultured cells are used to reconstruct a tissue or organ in vitro.

As used herein, the term "NIKS cells" refers to cells having the characteristics of the cells deposited as cell line ATCC CRL-12191.

As used herein, the term "stem cells" refers to undifferentiated cells that can give rise to a succession of mature functional cells.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "mixed cell culture" refers to a culture comprising cells derived from greater than one (e.g., two) species of organisms.

As used herein, the term "species specific nucleic acid" refers to nucleic acid (e.g., genomic DNA) derived from a specific organism. In some embodiments, species specific nucleic acid is present in a mixed cell culture that comprises species specific nucleic acid derived from a second organism.

As used herein, the term "genome" refers to the genetic material (e.g., chromosomes) of an organism.

The term "nucleotide sequence of interest" refers to any nucleotide sequence (e.g., RNA or DNA), the manipulation of which may be deemed desirable for any reason (e.g., treat disease, confer improved qualities, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "nucleic acid derived from" as in "nucleic acid derived from said first species" or "nucleic acid derived from said second species" refers to nucleic acid (e.g., preferably genomic DNA) native to a particular species of organism. In some embodiments, the nucleic acid is isolated (e.g., purified). In other embodiments, it is present in a cell lysate or extract of a single or mixed cell culture. In still further embodiments, it is present as a contaminant in a culture or sample of another species of nucleic acid.

As used herein, the term "repetitive element" refers to a region of genomic DNA that is present in at least 20, preferably at least 40, even more preferably at least 60, still more preferably at least 80, and yet more preferably, at least 100 copies in the genome of an organism.

As used herein, the term "protein of interest" refers to a protein encoded by a nucleic acid of interest.

As used herein, the term "exogenous gene" refers to a gene that is not naturally present in a host organism or cell, or is artificially introduced into a host organism or cell.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "homology" and "percent identity" when used in relation to nucleic acids refer to a degree of complementarity. There may be partial homology (i.e., partial identity) or complete homology (i.e., complete identity). A partially complementary sequence is one that at least partially inhibits a completely complementary sequence from hybridizing to a target nucleic acid sequence and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of primers and enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228: 227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target".

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification, amplification and isolation of particular gene sequences. In some embodiments, "probes" are PCR primers.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the term "multiplex PCR" refers to a PCR reaction that concurrently amplifies greater than one (e.g., two or more) different nucleic acid sequences of interest in the same reaction vessel. In some embodiments, the nucleic acid sequences are different regions of the same target sequence.

As used herein the term, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

As used herein, the term "purified" refers to molecules, either nucleic or amino acid sequences that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

DETAILED DESCRIPTION

The present invention relates to methods and compositions for the identification of species-specific material in pharmaceutical products. In particular, the present invention relates to methods for the identification of species-specific DNA in a population of a different species or following contact (e.g., growth) with cells of a different species.

I. Detection of Species-Specific Nucleic Acid

In some embodiments, the present invention provides methods of detecting species-specific DNA (e.g., mouse or rat DNA) in a mixed culture (e.g., human and non-human cell mixed culture) or previously in contact with DNA, cell products, or cells from another species. The DNA to be detected is not limited to DNA derived from cells present in a mixed culture. The methods are also applicable to DNA from cells that have been in contact with cell from another species, but are not longer in contact (e.g., DNA stuck to the outsides of the primary cell type or internal (e.g., episomally) within the primary cells).

For example, in some embodiments, the present invention provides methods of detecting contaminating DNA in cultures of cells grown on feeder cells (e.g., human cells grown on mouse feeder cells). Examples of cells grown on feeder cells include, but are not limited to, keratinocytes and stem cells (e.g., embryonic or adult stem cells). In other embodiments, the present invention provides methods of detecting contaminating DNA of a different species in cultures of cells cultures in the presence of whole or partial cell extracts or commercially available tissue culture plates coated with matrix proteins that may contain contaminating nucleic acid.

In other embodiments, the present invention provides methods of detecting degradation or inactivation of species-specific DNA (e.g., a mouse cell derived therapeutic present in a non-mouse cell host).

provide quantitative or semi-quantitative measures of the amount of species specific DNA in a cell culture of another species (See e.g., Example 6).

Primers utilized in the diagnostic methods of the present invention are preferably species-specific. In some preferred embodiments, primers are designed to repetitive species-specific nucleic acid sequences. In preferred embodiments, the repetitive element is present in at least 20, preferably at least 40, even more preferably at least 60, still more preferably at least 80, and yet more preferably, at least 100 copies. The detection of repetitive elements allows for an amplification of the detection signal.

For example, in some embodiments, primers are designed to a region of mouse-specific genomic DNA (MacGregor, H. C. and Varley, J. M. (1988). "Working with Animal Chromosomes," $2^{nd}$ ed., Wiley, N.Y. and Boyle and Ward, Genomics 12:517 [1992]). In some embodiments, primers are designed to a 15.6 kb element that is present in between 60 and 80 copies on mouse chromosome 8. Exemplary primer pairs include, but are not limited to, Chroma86 fwd (ST051)

```
5'GAATTCACTATGAAAGTCAGATTAGATC-3'                    (SEQ ID NO: 1) and Chroma86 rev (ST052) 5'-GAATTCCATAACCATTACAGTTGGCCAACC-3';        (SEQ ID NO: 2)

Chroma81 fwd (ST053) 5'-TGTAATAACAATGTCTGGACTTG-3'   (SEQ ID NO: 5)

and Chroma81 rev (ST054) 5'-TATGCAGCATATTTCTCTCAGTG-3'; (SEQ ID NO: 6)

fwd 5'-GAATTCGGGCAGAGCTGCTGGTCGAAT-3'                (SEQ ID NO: 7) and rev

5'-GAATTCTGAAGGTGGCCCCAGTGGTTTG-3'.                  (SEQ ID NO: 8)
```

A. Detection Methods

The present invention provides methods of detecting species-specific nucleic acid (e.g., present in a mixed cell culture). The methods of the present invention are robust and sensitive and are able to identify trace amounts of species-specific DNA in a population of a different species or following contact (e.g., growth) with DNA of a different species.

Cells grown on feeder cell layers (e.g., mouse or rat feeder cell layers) may be separated from feeder cells using methods well known in the art. In some embodiments (e.g., detection of species-specific DNA in human skin equivalents), samples of the cell culture are obtained via biopsy samples (e.g., punch biopsy). Samples for analysis are not limited to biopsy samples and may be obtained using any suitable method. Nucleic acids are next extracted from the sample for use in the diagnostic methods of the present invention. Nucleic acids may be isolated from cell and tissue samples using methods well known in the art (See e.g., the latest edition of Sambrook et al., Molecular Cloning: A Laboratory Manual, Cold Spring Harbor Press, NY).

1. PCR Detection

In some preferred embodiments, the methods of the present invention utilize PCR. In some embodiments, mouse-specific primers are combined with optimized assay conditions that allow for the detection of low levels of species specific DNA in a cell population of a different species (See Examples 4 and 6). In some embodiments, the PCR assay of the present invention further provides an internal control for the primary species (e.g., human or primate) DNA (See Example 2). In additional embodiments, primers do not demonstrate cross-reactivity with DNA from other species (See Example 7). In preferred embodiments, the methods of the present invention In other embodiments, primers are designed to human, rat and porcine genomic DNA sequences. In some embodiments, human primers are designed to a repetitive element in human DNA that is present at a copy number of approximately 800-1000 times (See e.g., PNAS USA Dec;81 (23): 7510-4; Genbank Accession #U01317) Exemplary human primers include, but are not limited to:

```
Human Primer Set 1:
Fwd 5'-TGTCAGGCCTCTGAGCCCAA-3'      (SEQ ID NO: 9)

Rev 5'-AGAGACTACCAAACAGGCTT-3'      (SEQ ID NO: 10)

Human Primer Set 2:
Fwd 5'-TTAACCTCCTATTTGACACC-3'      (SEQ ID NO: 11)

Rev 5'-AGATGGATCTCTTCCTGCGT-3'      (SEQ ID NO: 12)

Human Primer Set 3:
Fwd 5'-GGAAAAGGTTCAGTGAAGAC-3'      (SEQ ID NO: 13)

Rev 5'-AGTGCTGGTCTGTTTCTCAG-3'      (SEQ ID NO: 14)
```

In yet other embodiments, rat primers are designed to a repetitive element in rat DNA that is present at a copy number of approximately 120,000 times (See e.g., FEBS Lett. 164 (1), 175-180 (1983). Genbank Accession #X00170; J. Biol. Chem. 1984 Aug. 25; 259 (16): 10481-92). Exemplary rat primers include, but are not limited to:

```
Rat Primer Set 1:
Fwd 5'-AGCTTTGCAGTTTTATGAGA-3'      (SEQ ID NO: 15)

Rev 5'-AGCTTAAGTCCAAGTGGATC-3'      (SEQ ID NO: 16)
```

```
-continued
Rat Primer Set 2:
Fwd 5'-TCCCATTTGTCGATTCTTGA-3'      (SEQ ID NO: 17)

Rev 5'-AAGGACCTCCACATCAAACC-3'      (SEQ ID NO: 18)

Rat Primer Set 3:
Fwd 5'-GGTGCTCTTACTAGGATATT-3'      (SEQ ID NO: 19)

Rev 5'-AGGAATCAGAGAAAGGACTG-3'      (SEQ ID NO: 20)
```

In still further embodiments, porcine primers are designed to a repetitive element in porcine DNA that is present at a copy number of several hundred (See e.g., Mol Cell Biol 3: 903-13 [1983]; Genbank Accession #M21057). Exemplary porcine primers include, but are not limited to:

```
Porcine Primer Set 1:
Fwd 5'-AAGCTTATCTTTCCTAATTA-3'      (SEQ ID NO: 21)

Rev 5'-GCTCGGGAGGCGGGAAAGGG-3'      (SEQ ID NO: 22)

Porcine Primer Set 2:
Fwd 5'-CCCGAGCTCCCTGCCCGGTC-3'      (SEQ ID NO: 23)

Rev 5'-CCATCCCCTGAGGGCCTGGT-3'      (SEQ ID NO: 24)

Porcine Primer Set 3:
Fwd 5'-GACCTTCCAGAAGTGGGCGG-3'      (SEQ ID NO: 25)

Rev 5'-GGGACCAAGGCTGACTAGGC-3'      (SEQ ID NO: 26)
```

In some embodiments, multiplex PCR reactions are utilized to amplify both nucleic acids from greater than one species (e.g., mouse and non-mouse nucleic acids) concurrently (See e.g., U.S. Pat. No. 5,882,856, herein incorporated by reference).

The present invention is not limited to PCR detection. The methods of the present invention are suitable for use with any hybridization based detection methods. The nucleic acid probes disclosed herein (e.g., SEQ ID NOs: 1-26) may be used for detection is a variety of hybridization based detection methods. Exemplary methods include, but are not limited to, those described below.

2. Direct Detection of Hybridization

In some embodiments, hybridization of a nucleic acid sequence probe of the present invention labeled with a suitable label (e.g., fluorescent or radioactive) to the target sequence of interest is detected directly by visualizing a bound probe in a Southern assay; See e.g., Ausabel et al. (eds.), Current Protocols in Molecular Biology, John Wiley & Sons, NY [1991]). In these assays, genomic DNA is isolated from samples (e.g., as described above). The DNA is then cleaved with a series of restriction enzymes that cleave infrequently in the genome and not near any of the markers being assayed. The DNA or RNA is then separated (e.g., on an agarose gel) and transferred to a membrane. A nucleic acid probe of the present invention is allowed to contact the membrane under conditions of low, medium, or high stringency. Unbound labeled nucleic acid is removed and the presence of binding is detected by visualizing the labeled probe.

3. Detection of Hybridization Using "DNA Chip" Assays

In some embodiments of the present invention, target sequences are detected using a DNA chip hybridization assay. In this assay, a series of nucleic acid probes of the present invention are affixed to a solid support. Each of the probes is designed to be unique to a given target sequence. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

In some embodiments, the nucleic acid to be analyzed is isolated, amplified and labeled (e.g., with a fluorescent dye). The labeled DNA is then incubated with the array using a fluidics station. The array is then inserted into a scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (labeled nucleic acid sequences) (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given target sequence are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize with complementary DNA in the test sample (e.g., a species specific nucleic acid). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or nonspecifically bound DNA back into solution away from the capture probes. In some embodiments, a laser-based fluorescence scanner is then used to detect binding.

In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its, reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction sites. For example, the A amidite is delivered only to the sites where amidite A is to be coupled during that synthesis step and so on. Common reagents and washes are delivered by flooding the entire surface and removing by spinning.

DNA probes unique for the target sequence of interest (e.g., species specific DNA) are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given target sequence. Batches of beads are combined to form a pool specific to the array. To perform an assay, the BEAD ARRAY is contacted with a prepared subject sample (e.g., DNA). Hybridization is detected using any suitable method.

4. Enzymatic Detection of Hybridization

In some embodiments of the present invention, hybridization is detected by enzymatic cleavage of specific structures (e.g., the INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with a fluorescent dye that is quenched by an internal dye. Upon cleavage, the de-quenched labeled product may be detected using a standard fluorescence plate reader.

The INVADER assay detects specific target sequences in unamplified genomic DNA. The isolated DNA sample is contacted with the first probe specific for the target sequence of interest and allowed to hybridize. Then a secondary probe, specific to the first probe, and containing a fluorescent label, is hybridized and the enzyme is added. Binding is detected by using a fluorescent plate reader and comparing the signal of the test sample to known positive and negative controls.

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLITAQ GOLD DNA polymerase. A probe, specific for a given target sequence, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label (e.g., a fluorescent label) to the nucleotide suspected of being at the target nucleic acid location. Incorporation of the label into the DNA can be detected by any suitable method (e.g., with a fluorimeter).

5. Other Detection Assays

The nucleic acid probes of the present invention find use in additional detection assays including, but not limited to, enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884 and 6,183,960, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (Barnay Proc. Natl. Acad. Sci USA 88, 189-93 (1991)); and sandwich hybridization methods (e.g., U.S. Pat. No. 5,288,609, herein incorporated by reference in its entirety).

In addition, the technologies available from a variety of commercial sources, including, but not limited to, Aclara BioSciences, Haywood, Calif.; Agilent Technologies, Inc., Palo Alto, Calif.; Aviva Biosciences Corp., San Diego, Calif.; Caliper Technologies Corp., Palo Alto, Calif.; Celera, Rockville, Md.; CuraGen Corp., New Haven, Conn.; Hyseq Inc., Sunnyvale, Calif.; Incyte Genomics, Palo Alto, Calif.; Applera Corp., Foster City, Calif.; Rosetta Inpharmatics, Kirkland, Wash.; and Sequenom, San Diego, Calif. are amenable to use with the probes of the present invention.

B. Kits for Detecting Species-Specific Nucleic Acids

The present invention also provides kits for detecting the presence of species-specific nucleic acids present in a cell sample. The diagnostic kits are produced in a variety of ways.

In some embodiments, the kits contain at least one reagent for specifically detecting a species-specific nucleic acid. For example, in some embodiments, the kits contain probes (e.g., PCR primers) for detecting species-specific nucleic acid present in low amounts in a sample that had previously been in contact with the species (e.g., cells grown on feeder cells). In some embodiments, the kits further comprise second probes (e.g., PCR primers) for detecting the presence of the cell sample.

In some embodiments, the kit contains instructions for using the kit for determining the presence of species-specific nucleic acids. In some embodiments, the kits include ancillary reagents such as buffering agents, nucleic acid stabilizing reagents, protein stabilizing reagents, and signal producing systems (e.g., florescence generating systems as Fret systems). The test kit may be packaged in any suitable manner, typically with the elements in a single container or various containers as necessary along with a sheet of instructions for carrying out the test. In some embodiments, the kits also preferably include a positive control sample.

In some embodiments, the instructions further comprise the statement of intended use required by the U.S. Food and Drug Administration (FDA) in labeling in vitro diagnostic products. The FDA classifies in vitro diagnostics as medical devices and required that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use, including photographs or engineering drawings, where applicable; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalency determination. Additional information is available at the Internet web page of the U.S. FDA.

II. Applications

The present invention further provides application for using the species-specific DNA detection-methods of the present invention. The present invention is not limited to a particular application. The below description provides several non-limiting exemplary applications.

A. Organotypic Cultures

In some embodiments, the present invention provides methods of detecting species-specific (e.g., mouse) nucleic acids in organotypic cultures (e.g., of human keratinocytes). Cultured keratinocytes find use as skin substitutes suitable for a variety of applications including, but not limited to, testing of potential skin irritants, drug screening (e.g., for drugs that target epithelial cancers), expression of exogenous genes, and skin grafts. Generally, any source of cells or cell lines that can stratify into squamous epithelia are suitable for such applications. Accordingly, the present invention is not limited to the use of any particular source of cells that are capable of differentiating into squamous epithelia. Indeed, the present invention contemplates the use of a variety of cell lines and sources that can differentiate into squamous epithelia, including both primary and immortalized keratinocytes. Sources of cells include keratinocytes and dermal fibroblasts biopsied from humans and cavaderic donors (Auger et al., In Vitro Cell. Dev. Biol.—Animal 36:96-103; U.S. Pat. Nos. 5,968, 546 and 5,693,332, each of which is incorporated herein by reference), neonatal foreskins (Asbill et al., Pharm. Research 17(9): 1092-97 (2000); Meana et al., Burns 24:621-30 (1998); U.S. Pat. Nos. 4,485,096; 6,039,760; and 5,536,656, each of which is incorporated herein by reference), and immortalized keratinocytes cell lines such as NM1 cells (Baden, In Vitro Cell. Dev. Biol. 23(3):205-213 (1987)), HaCaT cells (Boucamp et al., J. cell. Biol., 106:761-771 (1988)); and NIKS cells (Cell line BC-1-Ep/SL; U.S. Pat. No. 5,989,837, incorporated herein by reference; ATCC CRL-12191).

In some embodiments, NIKS cells are utilized (See e.g., U.S. Pat. Nos. 6,214,567 and 5,989,837; each of which is herein incorporated by reference). The NIKS keratinocyte cell line, identified and characterized at the University of Wisconsin, is nontumorigenic and exhibits normal differentiation both in monolayer and organotypic culture. NIKS cells form fully stratified skin equivalents in culture. These cultures are indistinguishable by all criteria tested thus far from organotypic cultures formed from primary human keratinocytes. Unlike primary cells however, the immortalized NIKS cells will continue to proliferate indefinitely. This provides an opportunity to genetically manipulate the cells and isolate new clones of cells with new useful properties (Allen-Hoffmann et al., J. Invest. Dermatol., 114(3): 444-455 (2000)).

The NIKS cells arose from the BC-1-Ep strain of human neonatal foreskin keratinocytes isolated from an apparently normal male infant. In early passages, the BC-1-Ep cells exhibited no morphological or growth characteristics that were atypical for cultured normal human keratinocytes. Cultivated BC-1-Ep cells exhibited stratification as well as features of programmed cell death. To determine replicative lifespan, the BC-1-Ep cells were serially cultivated to senescence in standard keratinocyte growth medium at a density of $3 \times 10^5$ cells per 100-mm dish and passaged at weekly intervals (approximately a 1:25 split). By passage 15, most keratinocytes in the population appeared senescent as judged by the presence of numerous abortive colonies that exhibited large, flat cells. However, at passage 16, keratinocytes exhibiting a small cell size were evident. By passage 17, only the small-sized keratinocytes were present in the culture and no large, senescent keratinocytes were evident. The resulting population of small keratinocytes that survived this putative crisis period appeared morphologically uniform and produced colonies of keratinocytes exhibiting typical keratinocyte characteristics including cell-cell adhesion and apparent squame production. The keratinocytes that survived senescence were serially cultivated at a density of $3 \times 10^5$ cells per 100-mm dish. Typically the cultures reached a cell density of approximately $8 \times 10^6$ cells within 7 days. This stable rate of cell growth was maintained through at least 59 passages, demonstrating that the cells had achieved immortality. The keratinocytes that emerged from the original senescencing population were originally designated BC-1-Ep/Spontaneous Line and are now termed NIKS. The NIKS cell line has been screened for the presence of proviral DNA sequences for HIV-1 as well as HPV-16 and HPV-31 using either PCR or Southern analysis. None of these viruses were detected. The NIKS cell line has been extensively screened for the presence of specific viral pathogens, including HIV-1, HIV-2, HTLV-1, HTLV-2, HBV, HCV, EBV, CMV, and B19 human parvovirus. None of these viruses were detected. In addition, examination of mice and embryonated eggs inoculated with NIKS™ cell extracts demonstrates that NIKS™ keratinocytes are free of unidentified viral adventitious agents. The NIKS™ cell line is also free of mycoplasma contamination as determined by Hoechst and broth culture.

Keratinocyte cultures grown on plastic substrata and submerged in medium replicate but exhibit limited differentiation. Specifically, human keratinocytes become confluent and undergo limited stratification producing a sheet consisting of 3 or more layers of keratinocytes. By light and electron microscopy there are striking differences between the architecture of the multilayered sheets formed in tissue culture and intact human skin. In contrast, organotypic culturing techniques allow for keratinocyte growth and differentiation under in vivo-like conditions. Specifically, the cells adhere to a physiological substratum consisting of dermal fibroblasts embedded within a fibrillar collagen base. The organotypic culture is maintained at the air-medium interface. In this way, cells in the upper sheets are air-exposed while the proliferating basal cells remain closest to the gradient of nutrients provided by diffusion through the collagen gel. Under these conditions, correct tissue architecture is formed. Several characteristics of a normal differentiating epidermis are evident. In both the parental cells and the NIKS cell line a single layer of cuboidal basal cells rests at the junction of the epidermis and the dermal equivalent. The rounded morphology and high nuclear to cytoplasmic ratio is indicative of an actively dividing population of keratinocytes. In normal human epidermis, as the basal cells divide they give rise to daughter cells that migrate upwards into the differentiating layers of the tissue. The daughter cells increase in size and become flattened and squamous. Eventually these cells enucleate and form cornified, keratinized structures. This normal differentiation process is evident in the upper layers of both the parental cells and the NIKS cells. The appearance of flattened squamous cells is evident in the upper layers of keratinocytes and demonstrates that stratification has occurred in the organotypic cultures. In the uppermost part of the organotypic cultures the enucleated squames peel off the top of the culture. To date, no histological differences in differentiation at the light microscope level between the parental keratinocytes and the NIKS keratinocyte cell line grown in organotypic culture have been observed.

B. Stem Cells

In other embodiments, the methods and compositions of the present invention are utilized to detect the presence of species-specific DNA in mixed cell culture (e.g., human or primate stem cells grown on mouse feeder cells). Stem cells (See e.g., U.S. Pat. Nos. 6,326,198, 6,245,566, and 6,200, 806, WO 00/27995, WO 00/73421, WO 01/68815, WO 01/96532, WO 00/12682, and WO 01/53465, each of which is herein incorporated by reference) are undifferentiated cells that can give rise to a succession of mature functional cells.

Stem cells have the capacity, upon division, for both self-renewal and differentiation into progenitors. Thus, dividing stem cells generate both additional primitive stem cells and somewhat more differentiated progenitor cells. In addition to the generation of blood cells, stem cells also may give rise to osteoblasts and osteoclasts, and cells of other tissues.

A variety of strategies have been proposed for providing stem cells. These strategies may be divided into two different groups—stem cells derived from embryonic sources and stem cells derived from adult sources. For example, a hematopoietic stem cell may give rise to any of the different types of terminally differentiated blood cells. Embryonic stem (ES) cells are derived from the embryo and are pluripotent, thus possessing the capability of developing into any organ or tissue type or, at least potentially, into a complete embryo. For example, U.S. Pat. No. 5,843,780 to Thompson describes the production of stem cell lines from human embryos. PCT publications WO 00/52145 and WO 01/00650 describe the use of cells from adult humans in a nuclear transfer procedure to produce stem cell lines.

Examples of adult stem cells include hematopoietic stem cells, neural stem cells, mesenchymal stem cells, and bone marrow stromal cells. These stem cells have demonstrated the ability to differentiate into a variety of cell types including adipocytes, chondrocytes, osteocytes, myocytes, bone marrow stromal cells, and thymic stroma (mesenchymal stem cells); hepatocytes, vascular cells, and muscle cells (hematopoietic stem cells); myocytes, hepatocytes, and glial cells (bone marrow stromal cells) and, indeed, cells from all three germ layers (adult neural stem cells).

In order to retain the stem cell phenotype during in vitro culture, stem cells are frequently cultured on a feeder layer of fibroblasts (such as murine 3T3 or STO cells, See e.g., Martin and Evans, Proc. Natl. Acad. Sci USA 72:1441-1445 [1975]). If the stem cells or tissues derived by differentiation of stem cells are later to be used in humans, it is desirable to determine if the cells contain contaminating mouse cells. The methods of the present invention are thus useful in the detection of mouse DNA in cultures of non-mouse (e.g., human) stem cell cultures.

C. Additional Applications

The present invention is not limited to the detection of species specific DNA in mixed cell cultures. The methods and compositions of the present invention find use in any application that requires the detection of species-specific nucleic acid (e.g., where nucleic acid from more than one cell type is present). For example, in some embodiments, the methods and compositions of the present invention are used in the detection and quantitation of mouse specific genomic DNA in mixed cell culture. In other embodiments, the methods and composition of the present invention are used to monitor the degradation of mouse DNA (e.g., mouse cells in culture). In yet other embodiments, the methods of the present invention are used to monitor replication inactivation (e.g., by quantitating the amount of nucleic acid in a culture over time). In still further embodiments, the methods and compositions of the present invention are used in the detection of mouse genetic identification markers. In certain embodiments, the methods and compositions of the present invention are used to detect DNA that is desired in a product or treatment (to monitor the persistence of cells used as a therapeutic agent).

EXPERIMENTAL

The following examples serve to illustrate certain preferred embodiments and aspects of the present invention and are not to be construed as limiting the scope thereof.

In the experimental disclosure which follows, the following abbreviations apply: M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml (milliliters); µl (microliters); cm (centimeters); mm (millimeters); µm (micrometers); nm (nanometers); °C. (degrees Centigrade); cDNA (copy or complimentary DNA); CS (calf serum); DNA (deoxyribonucleic acid); ssDNA (single stranded DNA); dsDNA (double stranded DNA); dNTP (deoxyribonucleotide triphosphate); RNA (ribonucleic acid); bp (base pairs); PBS (phosphate buffered saline); g (gravity); OD (optical density).

EXAMPLE 1

Detection of Mouse Specific DNA using Mouse Primers ST051 and ST052

This example describes the detection of mouse specific DNA using the mouse primers ST051 and ST052. Genomic DNA was isolated from mouse (3T3-M1) and normal human dermal fibroblast (NHDF) cells for use as PCR templates. PCR primers ST051 (5'-GAATTCACTATGAAAGTCA-GATTAGATC-3'; SEQ ID NO:1) and ST052 (5'-GAATTC-CATAACCATTACAGTTGGCCAACC-3'; SEQ ID NO:2) were designed to amplify a 285 base pair (bp) product specific to mouse genomic DNA (MacGregor, H. C. and Varley, J. M. (1988). "Working with Animal Chromosomes," $2^{nd}$ ed., Wiley, N.Y.).

PCR reactions contained Mouse cell (3T3-M1) genomic DNA (123 ng/reaction) or Human cell (NHDF) genomic DNA (100 ng/reaction). Following Denaturation at 95° C. for 4 minutes, samples were subjected to the following for 35 cycles: Denaturation at 94° C. for 1 minute, Annealing at 50° C. for 1 minute, Extension at 72° C. for 2 minutes. A final Extension at 72° C. for 7 minutes was followed by a 4° C. Hold.

The 285 bp product amplified well when mouse (3T3-M1) genomic DNA was tested with mouse specific DNA primers ST051 and ST052. At the same time no PCR product was detected in human cell (NHDF) genomic DNA sample when assayed with mouse specific DNA primers.

EXAMPLE 2

Detection of Human specific DNA using Control PCR Primers ST047 and ST035

This Example describes the use of a second set of primers (ST047 (5'-GCCCGGCCCCTCTTGTCCCC-3'; SEQ ID NO:3) and ST035 (5'-GAGCCGGGGTCATCCGGTG-3'; SEQ ID NO:4) to amplify a 500 bp specific product from human genomic DNA. This example also describes the systematic evaluation and identification of optimal primer-template annealing conditions for both mouse and control PCR primer sets.

PCR reactions contained either Human genomic DNA (Promega, Madison, Wis.) (0.5 µg/reaction), Mouse cell (3T3) genomic DNA (250 pg/reaction), or Human genomic DNA (Promega) (0.5 µg/reaction)+Mouse cell (3T3) genomic DNA spike (250 pg/reaction). Following a Denaturation at 95° C. for 5 minutes, samples were subjected to the following for 30 cycles: Denaturation at 94° C. for 1 minute, Annealing conditions range 50° C.-70° C. for 1 minute, Extension at 72° C. for 2 minutes. A final Extension at 72° C. for 7 minutes was followed by a 4° C. Hold.

Primers ST047 and ST035 serve as a control PCR primer set used to verify the integrity of template genomic DNA for its ability to be PCR amplified. These control primers produce different size PCR products that correspond to each of the different species of genomic DNA tested. Expected PCR primer control product sizes are as follows—400 bp (mouse), 500 bp & 300 bp (human).

Primers ST047 and ST035 specifically amplified the expected 500 bp and 300 bp PCR product from human genomic DNA template. And as expected, these primers amplified a 400 bp PCR product from mouse genomic DNA template. PCR primers ST051 and ST052 specifically amplified a 285 bp PCR product from a mouse genomic DNA template. Band intensity remained relatively constant with or with out the addition of a (0.5 µg) human genomic DNA spike.

Optimal annealing temperatures of 57.3° C. and 68.6° C. were identified for the respective mouse specific and human PCR primer sets.

EXAMPLE 3

PCR using Skin Culture Biopsy Samples

This Example describes the isolation of genomic DNA from STRATAGRAFT (Stratatech Corp., Madison, Wis.) biopsy samples for evaluation as a genomic DNA template source in the PCR assays described in Examples 1 and 2. Total Genomic DNA was isolated from pooled (2) biopsy punches from the same STRATAGRAFT and used as a template for PCR amplification using control primers ST047 and ST035.

Genomic DNA Templates for PCR Reactions were one of the following:

Mouse cell (3T3) genomic DNA

Human cell (NIKS) genomic DNA

Human genomic DNA (Promega) (0.5 µg/reaction)

Human genomic DNA (Promega) (0.5 µg/reaction)+Mouse cell (3T3) genomic DNA spike (range 10-250 pg/reaction)

STRATAGRAFT genomic DNA (0.5 µg/reaction)

Following a Denaturation at 95° C. for 5minutes, samples were subjected to the following for 30 cycles: Denaturation at 94° C. for 1 minute, Annealing at 57.3° C. for 1 minute, Extension at 72° C. for 2 minutes. A final Extension at 72° C. for 7 minutes was followed by a 4° C. Hold.

The amount and integrity of genomic DNA isolated from STRATAGRAFT biopsy samples was found to be sufficient for analysis in a PCR assay. Control primers demonstrated the ability to amplify human genomic sequences from STRATAGRAFT biopsy genomic DNA. These results confirm the use of these control primers as reliable internal PCR control to validate amplification of genomic DNA samples.

EXAMPLE 4

Evaluation of Mouse-Specific DNA Detection Limits

This Example describes the evaluation of mouse specific DNA detection limits of this assay in a PCR reaction containing 0.5 µg of total human genomic DNA.

Genomic DNA Templates for PCR Reactions were one of the following:
Human genomic DNA (Promega) (0.5 µg/reaction)
Mouse cell (3T3) genomic DNA (123 ng/reaction)
Human genomic DNA (Promega) (0.5 µg/reaction)+Mouse cell (3T3) genomic DNA spike (range 25-500 pg/reaction)

Mouse specific PCR primers ST051 and ST052 were used. Following a Denaturation at 95° C. for 4 minutes, samples were subjected to the following for 30 cycles: Denaturation at 94° C. for 1 minute, Annealing at 55° C. for 1 minute, Extension at 72° C. for 2 minutes. A final Extension at 72° C. for 10 minutes was followed by a 4° C. Hold.

The results indicated that the mouse DNA detection limit is 250 pg of mouse genomic DNA in a PCR reaction containing 0.5 µg total human genomic DNA. Modification of the specific PCR assay conditions (e.g., number of cycles) may be utilized to improve the specified mouse DNA limit of detection.

EXAMPLE 5

Assay Variability and Reproducibility

This example describes an investigation of assay variability and reproducibility on the following:
1) Multiple biopsy DNA preparations from the same STRATAGRAFT sample.
2) Multiple STRATAGRAFT samples from the same production batch.
3) Multiple samples from the same batch of STRATAGRAFT by different production operators.

Genomic DNA Templates for PCR Reactions were one of the following:
STRATAGRAFT Genomic DNA (0.5 µg/reaction)
Human genomic DNA (Promega) (0.5 µg/reaction)
Human genomic DNA (Promega) (0.5 µg/reaction)+Mouse cell (3T3) genomic DNA spike (100 or 250 pg/reaction)

Mouse specific PCR primers ST051 and ST052 were used, in addition, control primers ST047 and ST035 were also used in parallel reactions.

Following Denaturation at 94° C. for 5 minutes, samples were subjected to the following for 30 cycles: Denaturation at 94° C. for 1 minute, Annealing at 61° C. for 1 minute, Extension at 72° C. for 2 minutes. A final Extension at 72° C. for 7 minutes was followed by a 4° C. Hold.

Only slight variability in the amount of the PCR product was detected as a result of multiple STRATAGRAFT DNA isolations, STRATAGRAFT preparations or STRATAGRAFT production operators. The observed PCR product variation is not significant and is expected as a normal result of a semi-quantitative PCR assay.

EXAMPLE 6

Titration of Mouse Cells

This example describes the verification of the detection limits that were previously calculated using mouse DNA equivalents by adding a known number of mouse 3T3-M1 cells to a predetermined number of NHDF cells. A decreasing percentage of mouse cells were titrated into a constant number of NHDF cells. Genomic DNA was isolated from these cell populations for subsequent PCR analysis. The intensities of the PCR products from the mixed-cell populations were compared to those obtained by mixing known amounts of mouse genomic DNA with human genomic DNA.

A semi-quantitative estimate of mouse cell specific DNA is based on $3.5 \times 10^{-12}$ g of mouse DNA per haploid chromosome set (MacGregor and Varley, 1988). Therefore, 250 pg of mouse genomic DNA equates to 35.7 mouse cell DNA equivalents. A human genomic DNA template sample of 0.5 µg is equivalent to 90,000 human cells.

Genomic DNA Templates for PCR Reactions were one of the following:
Mixed cell (NHDF/3T3-M1) population genomic DNA (0.5 µg/reaction)
Human cell (NHDF) genomic DNA (0.5 µg/reaction)
Mouse cell (3T3) genomic DNA (0.5 µg/reaction)
Human genomic DNA (Promega) (0.5 µg/reaction)
Human genomic DNA (Promega) (0.5 µg/reaction)+Mouse cell (3T3) genomic DNA (3.1-250 pg/reaction)

Mouse specific PCR primers ST051 and ST052 were used, in addition, control primers ST047 and ST035 were also used in parallel reactions. Following Denaturation at 95° C. for 5 minutes, samples were subjected to the following for 30 cycles: Denaturation at 94° C. for 1 minute, Annealing at 61° C. for 1 minute, Extension at 72° C. for 2 minutes. A final Extension at 72° C. for 7 minutes was followed by a 4° C. Hold.

The intensity of the PCR products obtained using DNA isolated from mixed-cell populations were comparable to the intensity obtained from mouse DNA equivalent spiked samples.

TABLE 1

Detection Results Using Spiked Mouse Cells

| Mouse Cell Number Spiked into 90,000 Human Cells | PCR Result |
| --- | --- |
| 265 cells | Detected |
| 132 cells | Detected |
| 66.1 cells | Detected |
| 13.2 cells | Detected |
| 6.6 cells | Detected |
| 3.3 cells | Detected |
| 0 (No Mouse Cells) | Non-Detected |

TABLE 2

Detection Results Using Spiked Isolated Mouse DNA

| Amount of Mouse Genomic DNA spiked into 0.5 µg human Genomic DNA | Approximate Cell Equivalents | PCR Result |
| --- | --- | --- |
| 250 pg | 36 | Detected |
| 125 pg | 18 | Detected |
| 62.5 pg | 9 | Detected |
| 12.5 pg | 2 | Detected |
| 6.25 pg | 1 | Non-Detected |
| 3.125 pg | 0.5 | Non-Detected |
| 0 (No Mouse DNA) | 0 | Non-Detected |

These results demonstrated the ability of the PCR assay able to detect less than four mouse cells in a background of approximately 90,000 human cells. Thus, this assay will detect low-level mouse cell contamination in the presence of human cells.

EXAMPLE 7

Cross-Reactivity of Mouse Specific Primers

This example demonstrates that no non-mouse DNA was detected with mouse-specific primers in non-mouse samples.

Genomic DNA Templates for PCR Reactions were one of the following:
Human genomic DNA (Promega) (0.5 µg/reaction)
Human genomic DNA (Clontech) (0.5 µg/reaction)
Rat genomic DNA (Clontech) (0.5 µg/reaction)
Rat genomic DNA (Stratatech) (0.5 µg/reaction)
Mouse genomic DNA (Clontech) (0.5 µg/reaction)
Mouse cell (3T3) genomic DNA (0.5 µg/reaction)
Mouse cell (3T3) genomic DNA (250 pg/reaction)
Mouse genomic DNA (Clontech) (250 pg/reaction)
STRATAGRAFT A Genomic DNA (0.5 µg/reaction)
STRATAGRAFT B Genomic DNA (0.5 µg/reaction)
Negative Control (No DNA)

Following Denaturation at 95° C. for 5 minutes, samples were subjected to the following for 30 cycles: Denaturation at 94° C. for 1 minute, Annealing at 61° C. for 1 minute, Extension at 72° C. for 2 minutes. A final Extension at 72° C. for 7 minutes was followed by a 4° C. Hold.

Mouse specific primers ST051 and ST052 demonstrated the absence of cross-reactivity or non-specific amplification of rat and human genomic DNA sequences. These primers are therefore specific to mouse genomic DNA sequences.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, biochemistry, or related fields are intended to be within the scope of the following claims.

We claim:

1. A method for detecting species-specific nucleic acid, comprising:
   a) providing
      i) a nucleic acid sample from a culture of cells of a first species, wherein said culture has had previous exposure to a second culture of cells from a second species or a cell product derived from said cells from a second species;
      ii) first nucleic acid probes specific for nucleic acid from said second species; and
      (iii) second nucleic acid probes specific for said first species;
   b) exposing said sample to said first nucleic acid probes under conditions such that said first nucleic acid probes hybridize to nucleic acid from said second species and do not hybridize to nucleic acid from said first species to detect nucleic acid from said second species; and
   c) exposing said sample to said second nucleic acid probes, wherein said second nucleic acid probes are selected from the group consisting of SEQ ID NO:3 and SEQ ID NO:4, under conditions such that said second nucleic acid probes hybridize to nucleic acid from said first species and do not hybridize to nucleic acid from said second species to detect nucleic acid from said first species.

2. The method of claim 1, wherein said first nucleic acid probes are specific for a repetitive element of nucleic acid in the genome of said second species.

3. The method of claim 2, wherein at least 20 copies of said repetitive element are present in the genome of said second species.

4. The method of claim 1, wherein said cells from a second species are selected from the group consisting of rat cells, mouse cells, and porcine cells.

5. The method of claim 1, wherein said exposing of b) and/or c) comprises PCR.

6. The method of claim 5, wherein said first nucleic acid probes and/or said second nucleic acid probes are PCR primers.

7. The method of claim 1, wherein said first nucleic acid probes and said second nucleic acid probes are PCR primers, and wherein said exposing of b) and c) comprises PCR, and wherein said PCR is a multiplex PCR reaction.

8. The method of claim 1, wherein said first nucleic acid probes are selected from the group consisting of SEQ ID NOs: 1, 2, and 5-26.

9. The method of claim 1, wherein said culture of cells of a first species is a cultured human skin tissue.

10. The method of claim 9, wherein said cultured human skin tissue comprises keratinocytes selected from the group consisting of primary keratinocytes and immortalized keratinocytes.

11. The method of claim 10, wherein said immortalized keratinocytes are NIKS cells.

12. The method of claim 1, wherein said culture of cells of a first species comprises stem cells.

13. The method of claim 1, wherein said cells from a second species comprise feeder cells.

14. The method of claim 13, wherein said feeder cells are mouse fibroblast cells.

15. A method for detecting species-specific nucleic acid, comprising:
   a) providing
      i) a nucleic acid sample from a culture of cells from a first species, wherein said culture has had previous exposure to a feeder layer from a second species;
      ii) first nucleic acid probes specific for nucleic acid derived from said feeder layer from said second species, wherein said first nucleic acid probes are selected from the group consisting of SEQ ID NOs: 1, 2, and 5-26; and
      iii) second nucleic acid probes specific for said first species selected from the group consisting of SEQ ID NO:3 and SEQ ID NO:4;
   b) exposing said sample to said first nucleic acid probes under conditions such that said first nucleic acid probes hybridize to nucleic acid derived from said feeder layer and do not hybridize to nucleic acid from said first species to detect nucleic acid from said second species; and c) exposing said sample to said second nucleic acid probes under conditions such that said second nucleic acid probes hybridize to nucleic acid from said first species and do not hybridize to nucleic acid from said second species to detect nucleic acid from said first species.

16. The method of claim 15, wherein said first nucleic acid probes are specific for a repetitive element of nucleic acid in the genome of said second species.

17. The method of claim 16, wherein at least 20 copies of said repetitive element are present in the genome of said second species.

18. The method of claim 15, wherein said feeder layer is a mouse cell feeder layer.

19. The method of claim 15, wherein said exposing of b) and/or c) comprises PCR.

20. The method of claim 19, wherein said first nucleic acid probes and/or said second nucleic acid probes are PCR primers.

21. The method of claim 15, wherein said first nucleic acid probes and said second nucleic acid probes are PCR primers, and wherein said exposing of b) and c) comprises PCR, and wherein said PCR is a multiplex PCR reaction.

22. The method of claim 15, wherein said culture of cells from a first species is a cultured human skin tissue.

23. The method of claim 22, wherein said cultured human skin tissue comprises NIKS cells.

* * * * *

```
                             SEQUENCE LISTING

<160> NUMBER OF SEQ ID NOS: 26

<210> SEQ ID NO 1
<211> LENGTH: 28
<212> TYPE: DNA
<213> ORGANISM: Artificial Sequence
<220> FEATURE:
<223> OTHER INFORMATION: Synthetic

<400> SEQUENCE: 1
gaattcacta tgaaagtcag attagatc                                          28

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
gaattccata accattacag ttggccaacc                                        30

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
gcccggcccc tcttgtcccc                                                   20

<210> SEQ ID NO 4
<211> LENGTH: 19
<212> TYPE: DNA
<213> ORGANISM: Artificial Sequence
<220> FEATURE:
<223> OTHER INFORMATION: Synthetic

<400> SEQUENCE: 4
gagccggggt catccggtg                                                    19
```

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
tgtaataaca atgtctggac ttg                                           23

<210> SEQ ID NO 6
<211> LENGTH: 23
<212> TYPE: DNA
<213> ORGANISM: Artificial Sequence
<220> FEATURE:
<223> OTHER INFORMATION: Synthetic

<400> SEQUENCE: 6
tatgcagcat atttctctca gtg                                           23

<210> SEQ ID NO 7
<211> LENGTH: 27
<212> TYPE: DNA
<213> ORGANISM: Artificial Sequence
<220> FEATURE:
<223> OTHER INFORMATION: Synthetic

<400> SEQUENCE: 7
gaattcgggc agagctgctg gtcgaat                                       27

<210> SEQ ID NO 8
<211> LENGTH: 28
<212> TYPE: DNA
<213> ORGANISM: Artificial Sequence
<220> FEATURE:
<223> OTHER INFORMATION: Synthetic

<400> SEQUENCE: 8
gaattctgaa ggtggcccca gtggtttg                                      28

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tgtcaggcct ctgagcccaa                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
agagactacc aaacaggctt                                               20

<210> SEQ ID NO 11
<211> LENGTH: 20
<212> TYPE: DNA
<213> ORGANISM: Artificial Sequence
<220> FEATURE:

-continued

<223> OTHER INFORMATION: Synthetic

<400> SEQUENCE: 11
ttaacctcct atttgacacc                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
agatggatct cttcctgcgt                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
ggaaaaggtt cagtgaagac                    20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
agtgctggtc tgtttctcag                    20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
agctttgcag ttttatgaga                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
agcttaagtc caagtggatc                    20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
tcccatttgt cgattcttga                    20

```
<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
aaggacctcc acatcaaacc                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
ggtgctctta ctaggatatt                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
aggaatcaga gaaaggactg                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
aagcttatct ttcctaatta                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
gctcgggagg cgggaaaggg                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
cccgagctcc ctgcccggtc                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 24 ccatccctg agggcctggt                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
gaccttccag aagtgggcgg                                                   20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
gggaccaagg ctgactaggc                                                   20
```